United States Patent
Chinnari et al.

(10) Patent No.: US 12,128,089 B2
(45) Date of Patent: Oct. 29, 2024

(54) STABLE LIQUID COMPOSITIONS OF GLUCAGON

(71) Applicant: Slayback Pharma LLC, Princeton, NJ (US)

(72) Inventors: Harish Govindaraja Setty Chinnari, Hyderabad (IN); Somashekhar Battini, Hyderabad (IN); Lourdu Chinnu Thippabattuni, Hyderabad (IN); Satheesh Balasubramanian, Hyderabad (IN); Sumitra Ashokkumar Pillai, Hyderabad (IN); Praveen Kumar Subbappa, Princeton, NJ (US)

(73) Assignee: SLAYBACK PHARMA LLC, Princeton, NJ (US)

( * ) Notice: Subject to any disclaimer, the term of this patent is extended or adjusted under 35 U.S.C. 154(b) by 0 days.

(21) Appl. No.: 18/202,103

(22) Filed: May 25, 2023

(65) Prior Publication Data
US 2023/0381282 A1    Nov. 30, 2023

(30) Foreign Application Priority Data
May 26, 2022   (IN) .............................. 202241030296

(51) Int. Cl.
| | | |
|---|---|---|
| A61K 38/26 | (2006.01) | |
| A61K 9/00 | (2006.01) | |
| A61K 9/08 | (2006.01) | |
| A61K 47/20 | (2006.01) | |
| A61K 47/26 | (2006.01) | |

(52) U.S. Cl.
CPC ............ *A61K 38/26* (2013.01); *A61K 9/0019* (2013.01); *A61K 9/08* (2013.01); *A61K 47/20* (2013.01); *A61K 47/26* (2013.01)

(58) Field of Classification Search
CPC .............................. A61K 38/26; C07K 14/605
See application file for complete search history.

(56) References Cited

U.S. PATENT DOCUMENTS

| | | | |
|---|---|---|---|
| 9,642,894 B2 | 5/2017 | Prestrelski | |
| 9,649,364 B2 | 5/2017 | Prestrelski et al. | |
| 11,590,205 B2 | 2/2023 | Prestrelski et al. | |
| 2011/0097386 A1* | 4/2011 | Steiner | A61P 3/08 514/11.7 |
| 2018/0236079 A1* | 8/2018 | Chen | A61K 47/10 |
| 2021/0030847 A1* | 2/2021 | Newswanger | A61K 38/26 |
| 2023/0192800 A1* | 6/2023 | Lim | A61K 47/10 514/7.2 |

FOREIGN PATENT DOCUMENTS

WO    WO-2019106586 A1 *  6/2019

OTHER PUBLICATIONS

Joshi et al., "The degradation pathways of glucagon in acidic solutions", International Journal of Pharmaceutics, 2000, vol. 203, pp. 115-125.

* cited by examiner

*Primary Examiner* — Jeffrey E. Russel
(74) *Attorney, Agent, or Firm* — Birch, Stewart, Kolasch & Birch, LLP

(57) ABSTRACT

Stable injectable compositions comprising glucagon or a pharmaceutically acceptable salt, solvate, or hydrate thereof are disclosed, which comprise (a) a therapeutically effective amount of glucagon; (b) at least one pharmaceutically acceptable solvent; (c) at least one stabilizing agent; (d) at least one sugar; and (e) optionally, at least one pharmaceutically acceptable excipient; wherein said injectable solution is stable and ready-to-use, and wherein pH of the said solution ranges from 3.8 to 4.2. Preferably, the composition is provided in a sealed container, e.g., an ampoule, a vial, a pre-filled syringe or an auto-injector. Further, stable injectable solutions are disclosed, which comprise glucagon or a pharmaceutically acceptable salt, solvate, or hydrate thereof, and which are suitable for subcutaneous, intravenous or intramuscular administration. Methods for manufacturing stable injectable solutions of glucagon are also disclosed.

20 Claims, No Drawings

Specification includes a Sequence Listing.

STABLE LIQUID COMPOSITIONS OF GLUCAGON

CROSS-REFERENCE TO RELATED APPLICATIONS

This application claims foreign priority to Indian Application No. IN 2022/41030296, filed on May 26, 2022, which is incorporated herein by reference in its entirety.

REFERENCE TO ELECTRONIC SEQUENCE LISTING

The application contains a Sequence Listing which has been submitted electronically in .XML format and is hereby incorporated by reference in its entirety. Said XML copy, created on May 24, 2023, is named "7077-0116PUS1.xml" and is 2,198 bytes in size. The sequence listing contained in this .XML file is part of the specification and is hereby incorporated by reference herein in its entirety.

FIELD OF THE INVENTION

The present invention relates to stable, injectable compositions comprising glucagon or a pharmaceutically acceptable salt, solvate, or hydrate thereof, preferably wherein the composition is provided in a sealed container, e.g., an ampoule, a vial, a pre-filled syringe, an auto-injector, etc. Further, the present invention relates to a stable injectable solution comprising glucagon or a pharmaceutically acceptable salt, solvate, or hydrate thereof, suitable for subcutaneous, intravenous, or intramuscular administration. The invention further relates to methods for manufacturing stable injectable solutions of glucagon.

BACKGROUND OF THE INVENTION

Glucagon is a polypeptide hormone secreted by the alpha cells of the Islets of Langerhans in the pancreas. It is a highly conserved polypeptide consisting of a single chain of 29 amino acids, with a molecular weight of 3485 Daltons.

Pharmacologically, glucagon increases the concentration of glucose in the blood. The first six amino acids at the N-terminus of the glucagon molecule bind to specific receptors on liver cells, which leads to an increase in the production of cAMP, which facilitates the catabolism of stored glycogen and increases hepatic gluconeogenesis and ketogenesis.

Medically, glucagon is used to treat hypoglycemia (characterized by lower-than-normal blood glucose concentrations). Hypoglycemia is common in Type-1 diabetic patients and insulin users. Mild hypoglycemia causes anxiety, sweating, tremors, palpitations, nausea, and pallor. In severe hypoglycemia, the brain is starved of the glucose it needs for energy, leading to seizures, coma or even death. Severe hypoglycemia is a life-threatening emergency that requires immediate medical intervention, for which the current standard of care is glucagon injection. The immediate pharmacologic result of glucagon injection is an increase in blood glucose at the expense of stored hepatic glycogen. The onset of action post injection is 5-20 minutes. Glucagon is degraded in the liver, kidney, and tissue receptor sites. The half-life of glucagon in plasma is 3 to 6 minutes, similar to that of insulin.

Glucagon is currently approved and marketed in the United States under the brand names GLUCAGEN®, GLUCAGON® Emergency Kit and GVOKE®.

GLUCAGEN® and GLUCAGON® Emergency Kits contains lyophilized glucagon powder which is to be reconstituted using a suitable diluent shortly before use, i.e., a two-part sterile vial, intended for immediate use following reconstitution. These are sold as a rescue kit and are available for intravenous, intramuscular, or subcutaneous administration. These kits contain 1 mg (1 unit) of glucagon, and 49 mg of lactose in a sterile vial. Further, hydrochloric acid may have been added during manufacture to adjust the pH of the glucagon. The diluent contains 12 mg/mL glycerine, water for injection and hydrochloric acid. The diluent is injected into the powder vial, gently swirled to dissolve the glucagon, then the glucagon solution is pulled back into the same syringe ready for injection. The pH of this solution is approximately 2.5 to 3.5. The recommended dose is typically 0.5-1 mg.

GVOKE® is a ready-to-use glucagon injection approved and marketed in the United States under presentations like vial and syringe kit, pre-filled syringe, and auto-injector (HYPOPEN®) for subcutaneous administration, available in 0.5 mg/0.1 mL or 1 mg/0.2 mL auto-injector or pre-filled syringe, and in 1 mg/0.2 mL vial and syringe kit. Each 0.2 mL of GVOKE® (auto-injector and pre-filled syringe) contains 1 mg of glucagon, 11.1 mg of trehalose dihydrate NF, and 1.2 mg of 1N sulfuric acid NF, in dimethyl sulfoxide diluent. Each 0.1 mL of GVOKE® (auto-injector and pre-filled syringe) contains 0.5 mg of glucagon, 5.6 mg of trehalose dihydrate NF, and 0.6 mg of 1N sulfuric acid NF, in dimethyl sulfoxide diluent, whereas each 0.2 mL of GVOKE® (Vial and Syringe Kit) contains 1 mg of glucagon, 11.1 mg of trehalose dihydrate NF, 5.8 mg of mannitol USP, and 1.32 mg of 1N sulfuric acid NF, and NF in dimethyl sulfoxide diluent.

GVOKE® is indicated for the treatment of severe hypoglycemia in pediatric and adult patients with diabetes ages 2 years and above. The recommended dose of GVOKE® in adults and pediatric patients aged 12 years and above is 1 mg administered by subcutaneous injection into lower abdomen, outer thigh, or outer upper arm. If there has been no response after 15 minutes, an additional 1 mg dose of GVOKE® may be administered. The recommended dose of GVOKE® in pediatric patients (aged 2 to under 12 years of age) is 1 mg (patients who weigh 45 kg or greater) or 0.5 mg (patients who weigh less than 45 kg), administered by subcutaneous injection. If there has been no response after 15 minutes, an additional weight appropriate dose of GVOKE® may be administered.

Glucagon is readily soluble (>10 mg/mL) in aqueous solutions at pH less than 3 or greater than 9, and has very low solubility (<0.1 mg/mL) in the pH range of 4 to 8 due to its isoelectric point of 7.1. It can form a gel in acidic aqueous conditions (pH 3-4) and precipitates within an hour of preparation in a neutral aqueous solution. It has a helical conformation in the crystalline state, while in dilute aqueous solutions it has a random coil conformation with 15% α-helix at the C-terminal end. Glucagon is known to self-associate at high concentrations and forms aggregates and gels at mild temperatures in acidic and basic solutions.

In addition to its physical instability, glucagon undergoes various types of chemical degradation. The chemical degradation of glucagon is rapid and complex. In aqueous solution, it rapidly degrades to form several degradation products. At least 16 degradation products of glucagon have been reported with the major degradation pathways being aspartic acid cleavage at positions 9, 15, and 21 and glutaminyl deamidation at positions 3, 20 and 24. See Kirsch, L. E., et al., International Journal of Pharmaceutics, 203:115-

125 (2000). The mechanisms of deamidation can involve either direct hydrolysis of the amide side chain or formation of a cyclic imide intermediate.

U.S. Pat. No. 9,649,364 discloses stable glucagon formulations of glucagon, comprising glucagon peptide, an ionization stabilizing excipient and an aprotic polar solvent, wherein the glucagon peptide or salt thereof is not prepared by drying in the presence of a non-volatile buffer having a pH of 2 to 4 to produce a glucagon peptide having a pH memory of 2 to 4.

There still exists a need to develop alternate stable injectable glucagon solution for human use, which are safe, therapeutically effective, ready to administer and with prolonged room temperature stability without any significant loss of potency.

There also exists a need for development of novel compositions of glucagon that are ready-to-use, which minimizes or prevents degradation of glucagon. There exists a need for developing stable, therapeutically effective, ready-to-use injectable solutions of glucagon suitable for human use.

It would also be desirable for inventive glucagon solutions to remain stable over relevant period of time under suitable storage conditions and to be suitable for administration by subcutaneous or other parenteral routes.

SUMMARY OF THE INVENTION

In one aspect, the present application relates to a stable solution of glucagon, which is suitable for injection. Preparing a stable injectable solution of glucagon is quite challenging due to the inherent aspartic acid cleavage and/or glutaminyl deamidation exhibited by glucagon. The present invention fulfils this need by developing stable injectable solutions of glucagon, and thus provides methods of efficient and safer use to achieve an improved standard of patient care.

In an aspect, the present application relates to a stable injectable solution, comprising: (a) a therapeutically effective amount of glucagon; (b) at least one pharmaceutically acceptable solvent; (c) at least one stabilizing agent; (d) at least one sugar; and (e) optionally, at least one pharmaceutically acceptable excipient; wherein the solution is a stable, ready-to-use injectable solution; and wherein the solution is suitable for parenteral administration.

In an aspect, the injectable solution has a pH ranging from 3.8 to 4.2, preferably 3.9 to 4.1. In another aspect, the injectable solution has a pH ranging from 3.9 to 4.0.

In an aspect, Glucagon (16-29) impurity is present in an amount less than 2% when stored at 25° C./60% RH for at least 6 months.

In an aspect, the injectable solution is stable for at least 6 months when stored at 25° C./60% RH.

In an aspect, the injectable solution has low impurities, e.g., a total amount of impurities in the composition is less than 5% when stored at 25° C./60% RH for at least 6 months.

In an aspect, the injectable solution after administration to a human patient, is bioequivalent to a commercially available comparative glucagon composition corresponding to GVOKE® (New Drug Application (NDA) Number 212097; and National Drug Code (NDC) Numbers 72065-120, 72065-121, 72065-130 & 72065-131).

In an aspect, the injectable solution has a concentration of glucagon in the composition from about 2.5 mg/mL to about 10 mg/mL, preferably a concentration of glucagon in the composition is 0.5 mg/0.1 mL.

In an aspect, the injectable solution according to claim 1, has at least one pharmaceutically acceptable solvent selected from dimethyl sulfoxide (DMSO), dimethylformamide (DMF), ethyl acetate, n-methyl pyrrolidone (NMP), 1-methyl-2-pyrrolidone, 1,3-dimethyl-2-imidazolidinone, dimethylacetamide (DMA), acetone, tetrahydrofuran, 1,4-dioxane, acetonitrile, and propylene carbonate or mixtures thereof. Preferably, the at least one pharmaceutically acceptable solvent is DMSO.

In an aspect, in the injectable solution, the at least one stabilizing agent is present in a concentration between 0.001 mM to 50 mM, preferably in a concentration between 0.001 mM to 10 nM, or preferably in a concentration less than 10 mM.

In an aspect, the at least one stabilizing agent is hydrochloric acid, phosphoric acid, nitric acid, hydrofluoric acid, hydrobromic acid, perchloric acid, or derivatives, or mixtures thereof. Preferably, the at least one stabilizing agent is hydrochloric acid.

In an aspect, the at least one stabilizing agent is glycine, ethylglycine, glycylglycine, alanine, B-alanine, valine, leucine, norleucine, isoleucine, serine, threonine, aspartic acid, glutamic acid, hydroxy glutamic acid, lysine, hydroxylysine, ornithine, arginine, methionine, asparagine, glutamine, taurine, creatinine, and ethylenediaminetetraacetic acid, trimethylglycine (betaine), glycine hydrochloride, trimethylglycine (betaine) hydrochloride, or mixtures thereof. Preferably, the at least one stabilizing agent is glycine hydrochloride.

In an aspect, in the injectable solution, the at least one sugar is trehalose.

In an aspect, in the injectable solution, the at least one pharmaceutically acceptable excipient is a stabilizing agent, a sugar, a starch, a sugar alcohol, a buffering agent, a tonicity contributing agent, a pH adjusting agent, an antioxidant, a chelating agent, a preservative or a mixture thereof.

In another aspect, the injectable solution is provided in a sealed container, e.g., selected from ampoules, vials, pre-filled syringes (PFS) and auto-injectors. Preferably, the container is a sealed pre-filled syringe. An aspect relates to a finished product, such as a sealed container comprising the injectable solution, wherein the sealed container is selected from an ampoule, a vial, a pre-filled syringe (PFS) or an auto-injector.

An aspect relates to a method of treatment, comprising administering a therapeutically effective amount of the injectable solution to a patient in need of treatment for Exercise-Induced Hypoglycemia ("EIH") in diabetes, Post-Bariatric Hepoglycemia ("PBH"), Congenital Hyperinsulinism ("CHI") or Non-Insulinoma Pancreatogenous Hypoglycaemia Syndrome ("NIPHS"). Preferably, the present invention relates to inventive solutions of glucagon, suitable for human use, for the treatment of severe hypoglycemia in pediatric and adult patients with diabetes ages 2 years and above.

In another aspect, the present invention relates to inventive solutions of glucagon, suitable for human use, as a diagnostic aid for use during radiologic examinations to temporarily inhibit movement of the gastrointestinal tract in adult patients.

In yet another aspect, the present invention relates to stable injectable solutions of glucagon, suitable for human use, with prolonged room temperature stability and without any significant loss of potency.

In yet another aspect, the present invention relates to stable injectable solutions of glucagon, suitable for human use, wherein said solution exhibits not more than about 10% loss of glucagon when stored at 25° C./60% RH for at least 6 months.

An aspect of the present invention relates to stable injectable solutions of glucagon and methods for preparing such solutions. In certain aspects, the inventive solutions are suitable for subcutaneous, intravenous, or intramuscular administration.

The inventive solutions according to the invention may be provided in the form of aqueous or non-aqueous solution.

The inventive compositions are advantageously ready-to-use (RTU) or ready-to-dilute (RTD). An aspect of the invention relates to stable ready-to-use or ready-to-dilute glucagon compositions suitable for parenteral administration.

In an aspect, stable solutions suitable for parenteral administration comprises (a) therapeutically effective amount of glucagon; (b) one or more pharmaceutically acceptable solvents; and (c) one or more pharmaceutically acceptable excipients.

In another aspect, stable solutions suitable for parenteral administration comprises (a) therapeutically effective amount of glucagon; (b) one or more pharmaceutically acceptable solvents; (c) one or more stabilizing agents and (d) optionally, one or more pharmaceutically acceptable excipients.

In another aspect, stable solutions suitable for parenteral administration comprises (a) therapeutically effective amount of glucagon; (b) one or more pharmaceutically acceptable solvents; (c) one or more stabilizing agents (d) one or more sugars and (e) optionally, one or more pharmaceutically acceptable excipients.

In another aspect, stable solutions suitable for parenteral administration comprises (a) therapeutically effective amount of glucagon; (b) one or more pharmaceutically acceptable solvents; (c) one or more stabilizing agents; (d) one or more sugars and (e) optionally, one or more pharmaceutically acceptable excipients, wherein glucagon is present at a concentration of about 1 mg/0.2 mL or more.

In an aspect, stable solutions of glucagon suitable for parenteral administration comprises (a) therapeutically effective amount of glucagon; (b) pharmaceutically acceptable solvent; and (c) one or more pharmaceutically acceptable excipients selected from the group consisting of stabilizing agents, sugars, starches, sugar alcohols, buffering agents, tonicity contributing agents, pH adjusting agents, antioxidants, chelating agents, and preservatives.

In another aspect, stable solutions of glucagon suitable for parenteral administration comprises (a) therapeutically effective amount of glucagon; (b) one or more pharmaceutically acceptable solvents; (c) one or more stabilizing agents; and (d) optionally, one or more other pharmaceutically acceptable excipients, wherein the solution has a pH in the range of about 3 to about 4.5, preferably pH in range of about 3.9 to about 4.0.

In another aspect, stable solutions of glucagon suitable for parenteral administration comprises (a) therapeutically effective amount of glucagon; (b) one or more pharmaceutically acceptable solvents; (c) one or more stabilizing agents; and (d) optionally, one or more other pharmaceutically acceptable excipients, wherein the solution is stable for at least 6 months when stored at 25° C./60% RH or 25° C./40% RH or 30° C./65% RH or 40° C./75% RH or 2° C.-8° C. conditions.

In another aspect, stable solutions of glucagon suitable for parenteral administration comprises (a) therapeutically effective amount of glucagon; (b) one or more pharmaceu-
tically acceptable solvents; (c) one or more stabilizing agents; and (d) optionally, one or more other pharmaceutically acceptable excipients, wherein in said stable solutions of glucagon are bioequivalent to a commercially available glucagon drug product GVOKE® (New Drug Application (NDA) Number 212097; and National Drug Code (NDC) Numbers 72065-120, 72065-121, 72065-130 & 72065-131).

In an embodiment, stable solution suitable for parenteral administration comprises (a) glucagon; (b) stabilizing agent; (c) solvent; (d) sugar; and (e) optionally, one or more additional pharmaceutically acceptable excipients.

In an aspect, stable solution suitable for parenteral administration comprises (a) glucagon; (b) glycine hydrochloride; (c) DMSO; (d) trehalose; and (e) optionally, one or more additional pharmaceutically acceptable excipients.

In another aspect, stable solution suitable for parenteral administration comprises (a) glucagon; (b) glycine hydrochloride; (c) DMSO; (d) trehalose; and (e) optionally, one or more additional pharmaceutically acceptable excipients, wherein the concentration of glycine hydrochloride is less than or equal to 10 mM.

In an aspect, stable solution suitable for parenteral administration comprises (a) glucagon; (b) hydrochloride; (c) DMSO; (d) trehalose; and (e) optionally, one or more additional pharmaceutically acceptable excipients.

In another aspect, stable solution suitable for parenteral administration comprises (a) glucagon; (b) hydrochloride; (c) DMSO; (d) trehalose; and (e) optionally, one or more additional pharmaceutically acceptable excipients, wherein the concentration of hydrochloride is less than or equal to 10 mM.

In an aspect, stable solution suitable for parenteral administration comprises (a) glucagon; (b) glycine hydrochloride; (c) DMSO; (d) trehalose; and (e) optionally, one or more additional pharmaceutically acceptable excipients, wherein the solution has a pH in the range of about 3 to about 4.5, preferably pH ranging from 3.8 to 4.2.

In certain aspects, the invention relates to methods for making a composition, which comprise: (i) a specified quantity of a sugar (e.g., trehalose dihydrate) was added to a pharmaceutically acceptable solvent (e.g., DMSO solution) in a suitable container (e.g., a beaker, etc.) and stirred under suitable conditions (e.g., for about 10 minutes at 250±50 rpm) to obtain a clear solution; (ii) a stabilizing agent (e.g., 1 mM glycine hydrochloride solution) is added to the solution formed in (i) (e.g., the trehalose—DMSO solution) with continuous stirring; (iii) Glucagon is added to the solution formed in (ii) (e.g., the above glycine hydrochloride-DMSO solution) and stirred under suitable conditions (e.g., for about 10 minutes at 250±50 rpm) to obtain a clear final solution. Optionally, a pH of the final solution is adjusted with hydrochloric acid.

DETAILED DESCRIPTION OF THE INVENTION

Unless defined otherwise, all the technical and scientific terms used herein have the same meanings as commonly known by a person skilled in the art. In the case that there is a plurality of definitions for the terms herein, the definitions provided herein will prevail.

Unless specified otherwise, all the percentages, portions and ratios in the present invention are on weight basis. Unless otherwise indicated, all numbers expressing quantities of ingredients, properties such as molecular weight, reaction conditions, and so forth used in the present specification and associated claims are to be understood as being modified in all instances by the term "about."

As used herein, the term "about" means having a value falling within an accepted standard of error of the mean when considered by one of ordinary skill in the art. Frequently, the term "about" refers to ±20%, preferably ±10%, and more preferably ±5% of the value or range to which it refers.

Unless indicated to the contrary, the numerical parameters set forth in the following specification and attached claims are approximations that may vary depending upon the desired properties sought to be obtained by the embodiments of the present invention. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

While compositions and methods are described herein in terms of "comprising" various components or steps, the compositions and methods can also "consist essentially of" or "consist of" the various components and steps.

As used herein, "a," "an," "the," "at least one," and "one or more" are used interchangeably. As used herein, the term "or" is generally employed in its usual sense including "and/or" unless the content clearly dictates otherwise.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

Glucagon is an anti-hypoglycemic agent and a gastrointestinal motility inhibitor used to treat severe hypoglycemia. Its molecular formula is $C_{153}H_{225}N_{43}O_{49}S$ with the following structure:

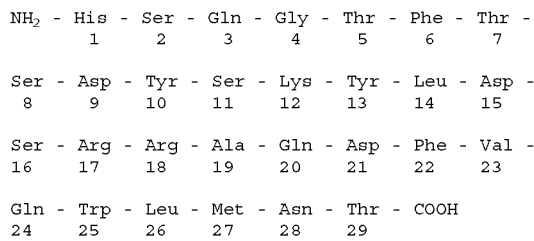

Glucagon

As used herein the term "glucagon" refers to glucagon free base or a pharmaceutically acceptable salt, solvate or hydrate thereof. In an aspect, all optically active amino acids may be in the L-configuration. It also includes geometric isomer or a stereoisomer thereof. The amount of glucagon may be expressed on an "Eq." basis. The "Eq." designation generally is used in connection with salt drug products to indicate that the strength of such drug product is being expressed in terms of the equivalent strength of the active moiety (e.g., on a basis of a free base), rather than in terms of the strength of the active ingredient taking into account the salt, etc.

Glucagon may be produced (but not limited to) by solid phase synthesis (synthetic) or expression of recombinant DNA in a *Saccharomyces cerevisiae* vector with subsequent purification.

The term "ready-to-use" or "RTU" encompasses within its scope, injectable compositions that are stable and does not require any reconstitution or dilution with parenterally acceptable diluent and can be directly administered to the patient.

The terms "parenterally acceptable liquid vehicle", "vehicle", "solvent", "pharmaceutically acceptable solvent" and "parenterally acceptable liquid solvent" may be interchangeable.

The terms "stable" and "stability" mean that the evolution of the product with time and/or under specific environmental conditions (i.e., temperature, humidity, etc.) has no significant effects on its quality, safety and/or efficacy for a given time period. It can be measured through the formation of degradation products (impurities), variation of pH, appearance (precipitation), microbial growth, and/or colour. The term "stable" indicates both chemical and physical stability. The term "stable" can further mean no more than about 30% loss of glucagon under typical commercial storage conditions. Preferably, formulations of the present inventions will have no more than about a 30% loss of glucagon, preferably, no more than about 20% loss of glucagon, more preferably, no more than about 10% loss of glucagon under typical commercial storage conditions (i.e., controlled room temperature or 25° C./60% RH or 25° C./40% RH or 2-8° C.).

The term "degradation product," as used herein, refers to an unwanted chemical or impurity (including, but not limited to known or unknown related substances) that can develop during the manufacturing, transportation, and storage of drug products and can affect the efficacy of pharmaceutical products. It can form in response to changes in light, temperature, pH, and humidity, or due to inherent characteristics of the active ingredient, such as their reaction with excipients or on contact with the packaging.

The term "parenteral" or "injectable" refers to routes selected from subcutaneous (SC), intravenous (IV), intramuscular (IM), intradermal (ID), intraperitoneal (IP) and the like.

The expression "bioequivalent" or "bioequivalence" is a term of art and is intended to be defined in accordance with Approved Drug Products with Therapeutic Equivalence Evaluations, 41th Edition, which is published by the U.S. Department of Health and Human Services, and is commonly known as the "Orange Book." Generally, bioequivalence can be defined as the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Bioequivalence of different formulations of the same drug substance involves equivalence with respect to the rate and extent of drug absorption. The pharmacokinetic characteristics of the concentration-time curve, such as the maximum observed plasma concentration ($C_{max}$), the time to reach $C_{max}$, and the area under the plasma concentration versus time curve (AUC), are examined by statistical procedures which are well-established in the field of pharmacokinetics. Two formulations (reference product and test product) whose AUC & Cmax differ by −20%/+25% or less are generally considered to be bioequivalent.

The term"bolus" or "bolus dose" refers to a discrete amount of a medication or a drug, e.g., glucagon, which is given within a specific time. The specific time over which the bolus dose is administered may be any suitable time which provides rapid onset of action (i.e., muscle relaxation). In some embodiments, the administration time may be about 6 minute or less.

The term "in vivo" in general means in the living body of a plant or animal, whereas the term "in vitro" generally means outside the body and in an artificial environment.

The term "subject" refers to an animal, including a human or non-human. The terms patient and subject may be used interchangeably herein. Non-human may be a rat, a dog, a mouse or a guinea pig.

The term "peak time of plasma drug concentration ($T_{max}$)" means the time when peak plasma drug concentration ($C_{max}$) is attained after drug administration.

The term "peak plasma drug concentration ($C_{max}$)" means the maximum plasma drug concentration attained after drug administration.

The term "$AUC_{0-infinity}$" means the areaa under a plasma drug concentration-time curve from time point of 0 to infinity after drug administration.

The term "$AUC_{0-t}$" means the area under a plasma drug concentration-time curve from time point of 0 to t after drug administration, wherein t is time in hours and is in between 1 hour to 72 hours.

The term "shelf life" means the period beginning from manufacture of a formulation beyond which the formulation cannot be expected beyond reasonable doubt to yield the therapeutic outcome approved by a government regulatory agency.

As used herein, the term "storage" refers to the holding of a composition under controlled or uncontrolled conditions for a period ranging from a few minutes to several months or longer. Storage conditions that can be controlled include, for example, temperature, humidity, and the level of light. In many cases, storage of a pharmaceutical formulation is under industry acceptable standards and/or standards that are mandated by regulatory agencies, such as USFDA.

As used herein, "significant loss of potency" can mean no more than about 30% loss of glucagon under typical commercial storage conditions (e.g., controlled room temperature or 25° C./60% RH or 25° C./40% RH or 2-8° C.).

The term "treatment" as used herein includes any treatment of a condition or disease in a subject, or particularly a human, and may include: (i) preventing the disease or condition from occurring in the subject, who may be predisposed to the disease but has not yet been diagnosed as having it; (ii) inhibiting the disease or condition, i.e., arresting its development; (iii) relieving the disease or condition, i.e., causing regression of the condition; or (iv) ameliorating or relieving the conditions caused by the disease, i.e., symptoms of the disease. "Treatment," as used herein, could be used in combination with other standard therapies or alone.

The term "effective amount" or "therapeutically effective amount" refers to an amount that is sufficient to effect treatment (e.g., to treat, prevent, or ameliorate a condition in a subject or patient), as defined herein, when administered to a subject in need of such treatment. The effective amount will vary depending on the subject and disease state being treated, the severity of the affliction and the manner of administration, and may be determined routinely by one of ordinary skill in the art. The effective amount of glucagon, used to practice the present invention for therapeutic management of a condition may be determined and adjusted by a person of ordinary skill to provide the appropriate amount and dosage regimen, e.g., depending upon one or more of the manners of administration, the age, body weight, sex, and/or general health of the patient.

Another objective of the present invention is to provide stable injectable solutions of glucagon when stored at room temperature for prolonged duration without significant loss of potency. Yet another objective of the present invention is to provide ready-to-use or ready-to-dilute stable injectable solutions of glucagon when stored at room temperature for prolonged duration without significant loss of potency.

In another embodiment, stable solutions of glucagon suitable for parenteral administration comprises (a) therapeutically effective amount of glucagon; (b) one or more pharmaceutically acceptable solvents; (c) one or more stabilizing agents; and (d) optionally, one or more other pharmaceutically acceptable excipients, wherein in said composition upon subcutaneous, intravenous or intramuscular administration exhibits bioequivalence to a commercially available reference glucagon solution product (such as GVOKE®), and wherein said bioequivalence is established by at least one of (i) a confidence interval for mean $AUC_{0-t}$ between about 80% and about 125%; (ii) a confidence interval for mean $AUC_{0-infinity}$ between about 80% and about 125%; (iii) a confidence interval for mean $C_{max}$ between about 80% and about 125% or a combination thereof.

The inventive solutions described herein may be provided in the form of a solution suitable for injection. To prepare such composition, the active drug is dissolved in a parenterally acceptable liquid vehicle. In certain non-limiting embodiments, a glucagon composition is formulated as a liquid and provided in the form of a solution. The pharmaceutically acceptable liquid vehicle or solvent may be selected from polar aprotic solvents include, but are not limited to dimethyl sulfoxide (DMSO), dimethylformamide (DMF), ethyl acetate, n-methyl pyrrolidone (NMP), 1-methyl-2-pyrrolidone, 1,3-dimethyl-2-imidazolidinone, dimethylacetamide (DMA), acetone, tetrahydrofuran, 1,4-dioxane, acetonitrile, and propylene carbonate or mixtures thereof. Particularly preferred polar aprotic solvents include dimethylacetamide, dimethyl sulfoxide, dimethylformamide and mixtures thereof.

The stable formulations of glucagon can be obtained by mixing a polar aprotic solvent, or a mixture of polar aprotic solvents, with a non-aqueous polar protic solvent or mixture of non-aqueous polar protic solvents. Pharmaceutically acceptable nonaqueous polar protic solvents are known in the art and include alkyl alcohols, for example, ethanol, ethylene glycol, propylene glycol, butylene glycol, glycerin, polysorbates, for example TWEEN 20, TWEEN 40, and TWEEN 80, and cyclodextrins (such as hydroxypropyl-β-cyclodextrin), polyalkylene glycols, such as polyethylene glycol, polypropylene glycol, and polybutylene glycol, and primary amides such as niacinamide. The certain embodiments, the polar aprotic solvent or aqueous polar protic solvent can be deoxygenated.

As used in herein, the terms glycerol, glycerin or glycerine can be used interchangeably, and refer to propane-1,2,3-triol.

In an embodiment of the invention, the ready-to-use or ready-to-dilute compositions may be formulated as non-aqueous solutions. Preferably, the ready-to-use or ready-to-dilute compositions will include a vehicle in an amount from about 0.05 mL to greater than or equal to 10 mL.

In an embodiment, stabilizing agents increase the stability of glucagon in pharmaceutical acceptable vehicle. In certain embodiments the stabilizing agent may be selected from mineral acids include, but are not limited to hydrochloric acid, phosphoric acid, nitric acid, hydrofluoric acid, hydrobromic acid, perchloric acid, or derivatives, and mixtures thereof. In other embodiments the stabilizing agent may be selected from organic acid such as an amino acid, amino acid derivative, or the salt of an amino acid or amino acid derivative include, but are not limited to glycine, ethylglycine, glycylglycine, alanine, B-alanine, valine, leucine, norleucine, isoleucine, serine, threonine, aspartic acid, glutamic acid, hydroxy glutamic acid, lysine, hydroxylysine, omithine, arginine, methionine, asparagine, glutamine, taurine, creatinine, and ethylenediaminetetraacetic acid, trimethylglycine (betaine), glycine hydrochloride, and trimethylglycine (betaine) hydrochloride, etc.

The formulation can comprise a stabilizing agent at a concentration of at least, at most, or about 0.001, 0.1, 0.5, 1, 5, 6, 7, 8, 9, 10, or 50 mM/mL to 10, 50, 75, 100, 500, 1000 mM/mL, or up to the solubility limit of the stabilizing agent in the aprotic polar solvent system. In certain embodiments, the stabilizing agent concentration is between 0.001 mM/mL to 50 mM/mL, preferably between 0.01 mM/mL to 50 mM/mL, preferably 0.1 mM/mL to 50 mM/mL, preferably 0.001 mM/mL to 10 mM/mL, preferably between 0.01 mM/mL to 10 mM/mL, or preferably 0.1 mM/mL to 10 mM/mL.

In certain non-limiting embodiments, glucagon is formulated as a composition, wherein glucagon is the only therapeutically active ingredient present in the composition. In another non-limiting embodiment, glucagon is formulated as a composition, wherein glucagon is formulated in combination with at least one or more other therapeutically active ingredients.

The present application relates to injectable solution of glucagon, particularly wherein glucagon is present at a concentration of 0.5 mg/0.1 mL or more. In another aspect, a stable ready-to-use solutions of the present invention comprises glucagon, wherein glucagon is present at concentration about 2.5 mg/mL to about 10 mg/mL, preferably 5 mg/mL.

Preferably, the stable ready-to-use solutions for human use will be provided as a solution dosage form that is suitable for subcutaneous or intravenous administration. The solutions may be formulated according to conventional pharmaceutical practice. The compositions of the invention can be administered in any conventional manner. It will be readily appreciated by those skilled in the art how to administer compositions of the present invention to a human.

In an embodiment, stable ready-to-use solution suitable for parenteral administration comprises (a) glucagon; (b) one or more pharmaceutical acceptable solvents selected from dimethyl sulfoxide (DMSO), dimethylformamide (DMF), ethyl acetate, n-methyl pyrrolidone (NMP), 1-methyl-2-pyrrolidone, 1,3-dimethyl-2-imidazolidinone, dimethylacetamide (DMA), acetone, tetrahydrofuran, 1,4-dioxane, acetonitrile, and propylene carbonate or suitable mixtures thereof; (c) one or more stabilizing agents selected from hydrochloric acid, phosphoric acid, nitric acid, hydrofluoric acid, hydrobromic acid, perchloric acid, or derivatives or mixtures thereof; (d) one or more sugars selected from trehalose, lactose, glucose, sucrose, inositol, fructose or combination thereof; (e) optionally, one or more additional pharmaceutically acceptable excipients.

In an embodiment, stable ready-to-use solution suitable for parenteral administration comprises (a) glucagon; (b) one or more pharmaceutical acceptable solvents selected from dimethyl sulfoxide (DMSO), dimethylformamide (DMF), ethyl acetate, n-methyl pyrrolidone (NMP), 1-methyl-2-pyrrolidone, 1,3-dimethyl-2-imidazolidinone, dimethylacetamide (DMA), acetone, tetrahydrofuran, 1,4-dioxane, acetonitrile, and propylene carbonate or suitable mixtures thereof; (c) one or more stabilizing agents selected from organic acid such as an amino acid, amino acid derivative, or the salt of an amino acid or amino acid derivative include, but are not limited to glycine, ethylglycine, glycylglycine, alanine, B-alanine, valine, leucine, norleucine, isoleucine, serine, threonine, aspartic acid, glutamic acid, hydroxy glutamic acid, lysine, hydroxylysine, ornithine, arginine, methionine, asparagine, glutamine, taurine, creatinine, and ethylenediaminetetraacetic acid, trimethyl glycine (betaine), glycine hydrochloride, and trimethyl glycine (betaine) hydrochloride, etc. or mixtures thereof; (d) one or more sugars selected from trehalose, lactose, glucose, sucrose, inositol, fructose or combination thereof; and (e) optionally, one or more additional pharmaceutically acceptable excipients.

In an embodiment, stable ready-to-use solution suitable for parenteral administration comprises (a) glucagon; (b) one or more pharmaceutical acceptable solvents (c) one or more sugars selected from trehalose, lactose, glucose, sucrose, inositol, fructose or combination thereof; (d) optionally, one or more additional pharmaceutically acceptable excipients, wherein the level of total impurities in solution is less than 30% as measured by HPLC when stored at 2-8° C., 25° C./60% RH or 25° C./40% RH conditions, preferably, wherein the level of total impurities in solution is less than 20% as measured by HPLC when stored at 2-8° C., 25° C./60% RH or 25° C./40% RH conditions, more preferably, wherein the level of total impurities in solution is less than 10% as measured by HPLC when stored at 2-8° C., 25° C./60% RH or 25° C./40% RH conditions.

In an embodiment, stable solution suitable for parenteral administration comprises (a) glucagon; (b) stabilizing agent; (c) solvent; (d) sugar; and (e) optionally, one or more additional pharmaceutically acceptable excipients.

In an embodiment, stable solution suitable for parenteral administration comprises (a) glucagon; (b) glycine hydrochloride; (c) DMSO; (d) trehalose; and (e) optionally, one or more additional pharmaceutically acceptable excipients.

In an embodiment, stable solution suitable for parenteral administration comprises (a) glucagon; (b) hydrochloric acid; (c) DMSO; (d) trehalose; and (e) optionally, one or more additional pharmaceutically acceptable excipients.

In an embodiment, stable solution suitable for parenteral administration comprises (a) glucagon; (b) hydrochloric acid or aspartic acid hydrochloride solution or glutamic acid hydrochloride solution; (c) DMSO; (d) trehalose; and (e) optionally, one or more additional pharmaceutically acceptable excipients.

The term "pharmaceutically acceptable excipient" as used herein means a diluent, carrier, or composition auxiliary, which is non-toxic and inert, which does not have undesirable effects on a subject to whom it is administered and is suitable for delivering a therapeutically active agent to the target site without affecting the therapeutic activity of the said active agent.

The inventive solutions of the present invention comprise one or more pharmaceutically acceptable excipient(s) selected from, but are not limited to, stabilizing agents, sugars, starches, sugar alcohols, water immiscible solvents, water, water miscible solvents, preservatives, chelating agents, antioxidants, tonicity contributing agents, anti-foaming agents, buffering agents, pH adjusting agents, surfactants, osmotic agents and the like or mixtures thereof.

The solutions of the present invention may contain other excipient is selected from sugars, starches, sugar alcohols. Examples of suitable sugars include, but are not limited to, trehalose, lactose, glucose, sucrose, inositol, fructose etc. Examples of suitable starches for stabilizing excipients include, but are not limited to, hydroxyethyl starch (HES). Examples of suitable sugar alcohols (also referred to as polyols) for stabilizing excipients include, but are not limited to, mannitol, xylitol, isomalt, maltitol and sorbitol.

The solutions of the present invention may additionally contain a buffering agent, which is used to resist change in pH upon dilution or addition of acid or alkali. Such compounds include, by way of example and without limitation, sodium dihydrogen phosphate monohydrate, disodium hydrogen phosphate anhydrous, acetic acid, sodium acetate, adipic acid, benzoic acid, sodium benzoate, monobasic sodium phosphate, dibasic sodium phosphate, disodium hydrogen phosphate dodecahydrate, lactic acid, tris buffer, tartaric acid, potassium metaphosphate, potassium phosphate, monobasic sodium acetate, sodium bicarbonate, sodium tartrate and others known to those of ordinary skill in the art.

The solutions of the present invention may additionally contain a "tonicity contributing agent" or a "tonicity adjusting agent" that can be used to adjust the tonicity of the liquid formulation. Suitable tonicity contributing agent include glycerine, lactose, mannitol, dextrose, sodium chloride, sodium sulphate, sorbitol, trehalose, xylitol, sucrose, maltose and others known to those or ordinary skill in the art. In one embodiment, the tonicity of the liquid formulation approximates that of the tonicity of blood or plasma. The amount of tonicity contributing agent may range from about 1 mg/mL to about 50 mg/mL of the composition.

The solutions of the present invention may additionally contain a chelating agent selected from the group consisting of ethylene-diaminetetraacetic acid (EDTA), diethylenetriaminepentaacetic acid (DTPA), ethylene glycol-bis (β-aminoethyl ether)-tetra acetic acid (EGTA), N-(hydroxyethyl) ethylene-diaminetriacetic acid (HEDTA), nitrilotriacetic acid (NTA), triethanolamine, 8-hydroxyquinoline, phosphoric acid, gluconic acid, saccharic acid, thiodipropionic acid, acetonic dicarboxylic acid, lecithin, di(hydroxyethyl) glycine, phenylalanine, tryptophan, glycerine, sorbitol and pharmaceutically acceptable salts thereof. More preferably, the chelating agent is selected from the group consisting of EDTA, DTPA, phosphoric acid, gluconic acid or a pharmaceutically acceptable salt thereof.

The solutions of the present invention may additionally contain an antioxidant which inhibits oxidation and thus is used to prevent the deterioration of preparations by the oxidative process. Such compounds include by way of example and without limitation, acetone, sodium bisulfate, ascorbic acid, ascorbyl palmitate, citric acid, L-cysteine hydrochloride, L-methionine, butylated hydroxy anisole, butylated hydroxytoluene, hydro phosphorous acid, monothioglycerol, propyl gallate, sodium ascorbate, sodium citrate anhydrous, sodium citrate dihydrate, sodium sulfide, sodium sulfite, sodium bisulfite, sodium formaldehyde sulfoxylate, thioglycolic acid, sodium metabisulfite and others known to those of ordinary skill in the all. The amount of antioxidant may be used in a suitable amount, e.g., an amount of the antioxidant may range from about 0.1 mg/mL to about 50 mg/mL of the composition.

The solutions of the present invention may additionally contain a preservative selected from the group consisting of ethanol, benzoic acid and the sodium or potassium salts thereof, sorbic acid and the sodium or potassium salts thereof, chlorobutanol, benzyl alcohol, phenyl ethanol, methyl, ethyl, propyl or butyl-p-hydroxybenzoates, phenol, m-cresol, p-chloro-m-cresol, phenylmercury nitrate or benzalkonium chloride.

The solutions of the present invention may additionally contain pH adjusting agents. The pH adjusting agents are selected from the group consisting of hydrochloric acid, sodium hydroxide, potassium hydroxide, magnesium hydroxide, sodium carbonate, tromethamine, sodium linoleate, sodium oleate, potassium carbonate, potassium linoleate, potassium oleate, and mixtures thereof. In one embodiment, solution comprising glucagon can be formulated at any suitable pH. The pH of the solution preferably ranges from about 3 to about 4.5, preferably from about 3.7 to about 4.3, most preferably about 4.0 when measured at room temperature. In one embodiment, solution comprising glucagon can be formulated using any suitable pH adjusting agent. In a preferred aspect, it is possible to maintain the pH of the said composition without using a suitable buffering agent.

The solutions of the present invention may additionally contain anti-foaming agents. The anti-foaming agents are selected from the group consisting of Sodium carboxymethylcellulose, sorbitol, mannitol, polyvinylpyrrolidone (PVP), polyoxyethylene sorbitan monolaurate or monooleate, polysorbates or Tween 20 and 80, polyoxyethylene/polyoxypropylene/polyoxyethylene copolymer (Pluronic L-62), glycerol polyethylene glycol ricinoleate (Cremophor EL), silicone antifoam (Dimethicone), sorbitan monooleate or monolaurate (Span 20 and 80), propylene glycol; polyethylene glycol 300 (PEG), ethanol, dimethyl acetamide (DMA), glycerol, N-methyl-2-pyrrolidone, and monothioglycerol.

According to yet another embodiment, the stable solution of glucagon suitable for parenteral administration comprising (a) therapeutically effective amount of glucagon; (b) pharmaceutically acceptable solvent; (c) one or more stabilizing agents; and (d) one or more other pharmaceutically acceptable excipients, wherein the solution is stable when stored at room temperature for prolonged duration without significant loss of potency.

According to yet another embodiment, the present invention provides stable injectable glucagon solutions at concentrations higher than 0.5 mg/0.1 mL and methods of preparing such solutions. In particular, the present invention provides stable injectable glucagon solutions at concentrations higher than 0.5 mg/0.1 mL and methods of preparing such solutions. In particular, the present invention provides stable aqueous glucagon solutions for parenteral administration at concentrations about 0.1 mg/0.1 mL, about 0.2 mg/0.1 mL, about 0.3 mg/0.1 mL, about 0.4 mg/0.1 mL, about 0.5 mg/0.1 mL, about 0.6 mg/0.1 mL, about 0.7 mg/0.1 mL, about 0.8 mg/0.1 mL, about 0.9 mg/0.1 mL and about 1 mg/0.1 mL.

According to yet another embodiment, the present invention provides stable injectable glucagon solutions at concentrations higher than 0.1 mg/mL and methods of preparing such solutions. In particular, the present invention provides stable injectable glucagon solutions at concentrations higher than 2 mg/mL and methods of preparing such solutions. In particular, the present invention provides stable aqueous glucagon solutions for parenteral administration at concentrations about 0.1 mg/mL, about 0.2 mg/mL, about 0.3 mg/mL, about 0.4 mg/mL, about 0.5 mg/ml, about 0.6 mg/mL, about 0.7 mg/mL, about 0.8 mg/mL, about 0.9 mg/mL, about 1 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg/mL, 4.8 mg/mL, 4.9 mg/mL, 5.0 mg/mL, 5.1 mg/mL, 5.1 mg/mL, 5.2 mg/mL, 5.3 mg/mL, 5.4 mg/mL, 5.5 mg/mL, 5.6 mg/mL, 5.7 mg/mL, 5.8 mg/mL, 5.9 mg/mL and 6.0 mg/mL.

The unit dose of the glucagon will be in the range from about 0.1 to about 10 mg. Exemplary unit dose of glucagon range from 0.1 mg to 10 mg, including unit dosages of 0.1 mg, 0.2 mg, 0.3 mg, 0.4 mg, 0.5 mg, 0.6 mg, 0.7 mg, 0.8 mg, 0.9 mg, 1 mg, 1.25 mg, 1.5 mg, 1.75 mg, 2 mg, 2.25 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8 mg, 8.25 mg, 8.5 mg, 8.75 mg, 9.0 mg, 9.25 mg, 9.5 mg, 9.75 mg and 10 mg wherein unit dose may be packed in vial, ampoule, pre-filled syringe, cartridge or auto-injector.

In certain embodiments, the invention relates to methods for making a composition, wherein: (i) trehalose dihydrate was added to the DMSO solution and stirred continuously until to obtain a clear solution; (ii) 1 mM glycine hydrochloride solution was added to the trehalose-DMSO solution with continuous stirring; and (iii) glucagon was added to the above glycine hydrochloride-DMSO solution and stirred until to get clear solution. Optionally, pH of final solution was adjusted with hydrochloric acid.

In certain embodiments, the invention relates to methods for making a composition, wherein: (i) Trehalose dihydrate was added to the DMSO solution in a beaker and stirred for about 10 minutes at 250±50 rpm to obtain a clear solution; (ii) 1 mM glycine hydrochloride solution was added to the trehalose-DMSO solution with continuous stirring; (iii) glucagon was added to the above glycine hydrochloride-DMSO solution and stirred for about 10 minutes at 250±50 rpm to obtain a clear solution. Optionally, the pH of final solutions was adjusted with hydrochloric acid.

Certain embodiments additionally relate to sterilizing the finished products, e.g., aseptic filtration-filling-sealing, terminal sterilization, incorporation of sterilizing agents, irradiation, and/or heating.

Sterilization may be accomplished by any of the conventional methods including aseptic filling, irradiation and heat sterilization. Heat sterilization is normally performed using steam, preferably wet steam to allow for the use of pressure as a means of temperature control. The time period for the sterilization must be long enough to meet the sterility requirements required of an injectable product. When steam is used, the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 5 to 15 minutes.

A pharmaceutically inert gas may be bubbled into the solution to drive out oxygen, which may be selected from nitrogen or carbon dioxide. Preferably, the solution is kept under nitrogen or carbon dioxide sparging until dissolved oxygen is less than 10 mg/L in the final solution.

Containers suitable according to the present invention are those known in the art. They include vials, cartridges, pre-filled syringes, auto-injectors, infusion bags, bottles and ampoule presentations. Containers may be fabricated from glass or from polymeric materials. Suitable containers should be of a size sufficient to hold one or more doses of glucagon.

The present invention provides for stable injectable glucagon solution in single-dose and/or multi-dose compositions. In some embodiments, the composition may be contained in vials, pre-filled syringes or auto-injectors. In some embodiments, the vials may be made from clear glass, amber glass, or plastic. In some embodiments, the vials or pre-filled syringes may be in the range of about 0.05 mL to 10 mL in volume, preferably in the range of about 0.05 mL to 5 mL, more preferably in the range of about 0.1 mL to 2 mL, and most preferably in the range of about 0.1 mL to 1 mL. In some embodiments, the composition may exist in a 0.1 mL or 0.2 mL single-dose pre-filled syringe. In some embodiments, the 0.1 mL or 0.2 mL vial may be a single-dose formulation.

The polymeric materials which may be used for such containers include, but are not limited to: polysulfone, polycarbonate, polypropylene, polyethylene (LDPE or HDPE), ethylene/propylene copolymers, polyolefins, acrylic-imide copolymers, polyester (e.g., PET, PEN and the like), Teflon, Nylon, acetal (Delrin), polymethyl pentene, PVDC, ethylvinylacetate, AN-copolymer etc. In addition, cyclic olefin copolymer (COC), crystal zenith (CZ) resin containers and similar resins can be used as rigid containers and syringes.

A ready-to-use pre-filled syringe comprising stable glucagon solution according to the invention will be advantageous, as compared to vials or ampoules. A pre-filled syringe fabricated from a polymer will not only be convenient for handling, storage and administration, but will also minimize mixing or dosing errors. The pre-filled syringe according to the invention may also include single use auto injectors and reusable auto injectors.

In one embodiment, the glucagon kit contains one (1) single-dose sterile syringe (29 G×½" needle) with markings for 0.1 mL (0.5 mg pediatric dose) and 0.2 mL, (1 mg adult dose), and one single-dose vial containing 0.2 mL of solution.

In some embodiments, the inventive glucagon composition disposed in a pre-filled syringe or auto-injector contains not more than about 30% total impurities after storage at 2-8° C. for at least 6 months as determined by HPLC, and in other embodiments the inventive glucagon composition disposed in a pre-filled syringe contains not more than about 30% impurities after storage at 2-8° C. for at least 6 months as determined by HPLC. In further embodiments, the inventive glucagon composition disposed in the pre-filled syringe contains not more than about 30% impurities after storage at 2-8° C. for at least 6 months as determined by HPLC.

In an embodiment, the inventive injectable solution comprising: (a) a therapeutically effective amount of glucagon; (b) at least one pharmaceutically acceptable solvent; (c) at least one stabilizing agent; (d) at least one sugar; and (e) optionally, one or more pharmaceutically acceptable excipients; wherein said solution is a stable and ready-to-use; and wherein pH of the said solution ranges from 3.8 to 4.2.

In an embodiment, stable ready-to-use solution in pre-filled syringe suitable for parenteral administration comprises (a) glucagon; (b) one or more pharmaceutical acceptable solvents; (c) at least one stabilizing agent; and (d) optionally, one or more additional pharmaceutically acceptable excipients, wherein the level of total impurities in solution is less than 30% as measured by HPLC when stored at 25° C./60% RH or 30° C./65% RH or 25° C./40% RH or 2-8° C. conditions for at least 6 months.

In an embodiment, stable ready-to-use solution in pre-filled syringe suitable for parenteral administration comprises (a) glucagon; (b) one or more pharmaceutical acceptable solvents; (c) at least one stabilizing agent; and (d) optionally, one or more additional pharmaceutically acceptable excipients, wherein the level of total impurities in solution is less than 20% as measured by HPLC when stored at 25° C./60% RH or 30° C./65% RH or 25° C./40% RH or 2-8° C. conditions for at least 6 months.

In an embodiment, stable ready-to-use solution in pre-filled syringe suitable for parenteral administration comprises (a) glucagon; (b) one or more pharmaceutical acceptable solvents; (c) at least one stabilizing agent; and (d) optionally, one or more additional pharmaceutically acceptable excipients, wherein the level of total impurities in solution is less than 10% as measured by HPLC when stored at 25° C./60% RH or 30° C./65% RH or 25° C./40% RH or 2-8° C. conditions for at least 6 months.

In an embodiment, stable ready-to-use solution in pre-filled syringe suitable for parenteral administration comprises (a) glucagon; (b) one or more pharmaceutical acceptable solvents; (c) at least one stabilizing agent; and (d) optionally, one or more additional pharmaceutically acceptable excipients, wherein the level of total impurities in solution is less than 5% as measured by HPLC when stored at 25° C./60% RH or 30° C./65% RH or 25° C./40% RH or 2-8° C. conditions for at least 6 months.

In an embodiment, stable ready-to-use solution in pre-filled syringe suitable for parenteral administration comprises (a) glucagon; (b) one or more pharmaceutical acceptable solvents; (c) at least one stabilizing agent; and (d) optionally, one or more additional pharmaceutically acceptable excipients, wherein the level of total impurities in solution is less than 5% as measured by HPLC when stored at 25° C./60% RH condition for at least 12 months.

In an embodiment, stable ready-to-use solution in pre-filled syringe suitable for parenteral administration comprises (a) glucagon; (b) one or more pharmaceutical acceptable solvents; (c) at least one stabilizing agent; and (d) optionally, one or more additional pharmaceutically acceptable excipients, wherein the level of Glucagon (16-29) impurity in solution is less than 5% as measured by HPLC when stored at 25° C./60% RH or 40° C./75% RH conditions for at least 6 months.

In an embodiment, stable ready-to-use solution in pre-filled syringe suitable for parenteral administration comprises (a) glucagon; (b) one or more pharmaceutical acceptable solvents; (c) at least one stabilizing agent; and (d) optionally, one or more additional pharmaceutically acceptable excipients, wherein the level of Glucagon (16-29) impurity in solution is less than 2% as measured by HPLC when stored at 25° C./60% RH condition for at least 12 months.

In an embodiment, stable ready-to-use solution in pre-filled syringe suitable for parenteral administration comprises (a) glucagon; (b) one or more pharmaceutical acceptable solvents; (c) at least one stabilizing agent; and (d) optionally, one or more additional pharmaceutically acceptable excipients, wherein the level of Glucagon (16-29) impurity in solution is less than 2% as measured by HPLC when stored at 25° C./60% RH condition for at least 12 months, wherein pH of said solution is ranges from 3.9 to 4.0.

In an embodiment, the present invention provides a kit comprising an auto injector which contains a pre-filled syringe (a pre-filled syringe assembled/placed in the auto injector). The autoinjector may be integrated with a needle stick protection feature and holds a pre-filled syringe containing a single dose, whereby the entire deliverable volume is expelled. The stable injectable glucagon solution preparations as described herein may further comprise effective amounts of one or more other therapeutically active ingredient.

Stability

As used herein, the term "stable" is defined as no more than about 30% loss of glucagon under typical commercial storage conditions. In certain embodiments, the compositions of the present invention will have no more than about 30% loss of glucagon, more preferably, no more than about 20% loss of glucagon, no more than about 10% loss of glucagon, under typical commercial storage conditions. The composition retains at least about 80% potency of glucagon after storing the composition at 25° C./60% RH or 25° C./40% RH or 30° C./65% RH or 40° C./75% RH for at least 6 months. In certain aspects, the term "stable" refers to chemical stability, wherein not more than 30% w/w of total related substances, preferably, not more than 20% w/w of total related substances, more preferably, not more than 10% w/w of total related substances are formed on storage at 2-8° C. for a period of at least six months or to the extent necessary for use of the composition.

Glucagon undergoes various types of chemical degradation. The chemical degradation of glucagon is rapid and complex. In aqueous solution, it rapidly degrades to form several degradation products. At least 16 degradation products of glucagon have been reported with the major degradation pathways being aspartic acid cleavage at positions 9, 15, and 21 and glutaminyl deamidation at positions 3, 20 and 24. See Kirsch, L E., et al., International Journal of Pharmaceutics, 203:115-125 (2000), which is hereby incorporated by reference in its entirety. The mechanisms of deamidation can involve either direct hydrolysis of the amide side chain or formation of a cyclic imide intermediate. Deamidation is a common protein degradation pathway that involves the loss of ammonia from the side chain amides of asparagine or glutamine to form the corresponding side chain carboxylic acid residues: aspartic or glutamic acid.

In an embodiment, the inventive solution are stable for at least 1 month at room temperature without significant loss of potency. In yet another embodiment, inventive solution are stable for at least 2 months at room temperature without significant loss of potency. In certain embodiments, the inventive solution are stable for at least 1 month when stored at 25° C. and 60% RH or 25° C./40% RH or 30° C./65% RH or 40° C./75% RH. In certain embodiments, the inventive solution are stable for at least 2 months when stored at 25° C. and 60% RH or 25° C./40% RH or 30° C./65% RH or 40° C./75% RH. In certain embodiments, the inventive solution are stable for at least 24 months when stored at 2-8° C.

In an embodiment, the inventive solution are stable for at least 1 month at room temperature with less than 20% loss of the active ingredient, preferably less than 10% loss of the active ingredient, preferably less than 5% loss of the active ingredient, or preferably less than 2% loss of the active ingredient. In yet another embodiment, inventive solution are stable for at least 2 months at room temperature with less than 20% loss of the active ingredient, preferably less than 10% loss of the active ingredient, preferably less than 5% loss of the active ingredient, or preferably less than 2% loss of the active ingredient. In certain embodiments, the inventive solution have this stability for at least 1 month when stored at 25° C. and 60% RH or 25° C./40% RH or 30° C./65% RH or 40° C./75% RH. In certain embodiments, the inventive solution have this stability for at least 2 months when stored at 25° C. and 60% RH or 25° C./40% RH or 30° C./65% RH or 40° C./75% RH. In certain embodiments, the inventive solution have this stability for at least 24 months when stored at 2-8° C.

In another embodiment, the stable injectable glucagon solution comprising glucagon is clear or free of any aggregates by visual inspection after storage for at least 1 month, for example, 2 months, 3 months, 6 months, 12 months, 18 months, or 24 months, at 2-8° C., 25° C./60% RH or 25° C./40% RH or 30° C./65% RH conditions.

General Characterization Methods of Glucagon:

| Parameter | Test methods |
|---|---|
| Primary structure (intact mass & sequence confirmation) | 1. MS, LC-MS and LC-MS/MS<br>2. NMR |
| Secondary structure & Higher order structure | 1. CD<br>2. FT-IR<br>3. 2D-NMR<br>4. Intrinsic Fluorescence |
| Impurity profiling | 1. UPLC - HRMS<br>2. UPLC-MS/MS<br>3. RP-HPLC |
| Oligomeric & Agglomeration Studies | 1. SV-AUC<br>2. SEC-MALS<br>3. AFM<br>4. Extrinsic Fluorescence |

In another embodiment of the invention, there is provided stable solution comprising glucagon for parenteral administration, wherein the solution does not contain more than 10% single maximum unknown impurity and/or does not contain more than 30% total impurities after storage for more than 1 month, for 3 months, for 6 months, for 12 months, for 18 months, for 24 months or for 36 months when stored at (i) 2-8° C. or (ii) 25±2° C. and 60±5% RH or (iii) 25±2° C. and 40±5% RH or (iv) 30° C./65% RH conditions. The parenteral solution comprising glucagon of the present invention does not form any precipitate and remains physically stable after storage for more than 2 months, for example, for 3 months, for 6 months, for 12 months, for 18 months, for 24 months or for 36 months when stored at (i) 2-8° C. or (ii) 25±2° C. and 60±5% RH or (iii) 25±2° C. and 40±5% RH or (iv) 30° C./65% RH conditions.

The following Table 1 displays relative retention time (RRT) and Mass Spectroscopy (MS) based identification of all impurity peaks detected above 0.1% peak area in inventive glucagon compositions at 40° C./75% RH.

TABLE 1

| RRT | Identification | Fragment sequence |
|---|---|---|
| 0.13 | Glucagon (22-29) | FVQWLMNT (residues 22-29 of SEQ ID NO: 1) |
| 0.31 | Glucagon (16-29) | SRRAQ DFVQWLMNT (residues 16-29 of SEQ ID NO: 1) |
| 0.49 | Glucagon (10-29) | YSKYLDSRRAQ DFVQWLMNT (residues 10-29 of SEQ ID NO: 1) |
| 0.82 | Glucagon dehydrated | — |
| 1.06 | (Glu3)-Glucagon | — |
| 1.29 | Glucagon (1-15) + Glucagon | HSQGTFTSDY SKYLD (residues 1-15 of SEQ ID NO: 1) + Glucagon |

TABLE 1-continued

| RRT | Identification | Fragment sequence |
|---|---|---|
| 1.41 | Glucagon (1-28), C-terminus-H2O isomer | — |

As summarized in Table 1, the major pathways of degradation include aspartic acid cleavage at positions 9, 15 and 21 and glutaminyl deamidation at positions 3, 20 and 24. Cleavage occurs on both sides of Asp-15, but only the C-terminal side of Asp-9 and Asp-21. The (Glu3)-Glucagon may correspond to a fragment where Gln-3 converted to Glu-3. With reference to glucagon (SEQ ID NO 1), Table 1 shows several of the corresponding fragment sequences:

(SEQ ID NO 1)
HSQGTFTSDY SKYLDSRRAQ DFVQWLMNT

In another embodiment, the shelf-life of a stable injectable solution comprising glucagon when stored at room temperature in the sealed original packaging may be between 1 month and 36 months, preferably between 6 months and 24 months.

Dosage and Administration

The inventive solution as described herein may be used for the treatment of severe hypoglycemia in pediatric and adult patients with diabetes ages 2 years and above. Further, the composition may be used as a diagnostic aid for use during radiologic examinations to temporarily inhibit movement of the gastrointestinal tract in adult patients.

Further, the inventive solution as described herein may be used for Exercise-Induced Hypoglycemia (EIH) in diabetes, Post-Bariatric Hypoglycemia (PBH), Congenital Hyperinsulinism (CHI) and Non-Insulinoma Pancreatogenous Hypoglycaemia Syndrome ("NIPHS").

For administration to human subjects, the inventive solutions comprise an effective dosage amount of glucagon. The formulation may be prepared using conventional methods, for example, depending on the subject to be treated, the mode of administration, and the type of treatment desired (e.g., prevention, prophylaxis, or therapy).

Preferably, the present application relates to method of using the inventive compositions for the treatment of severe hypoglycemia in pediatric and adult patients with diabetes ages 2 years and above, wherein the inventive composition comprises glucagon.

In one embodiment, the inventive solutions of the present invention can be supplied in the form of auto-injector, pre-filled syringe, and vial and syringe kit are for subcutaneous injection only.

In one embodiment, for adults and pediatric patients aged 12 and older, the recommended dose of glucagon is 1 mg administered by subcutaneous injection into lower abdomen, outer thigh, or outer upper arm. If there has been no response after 15 minutes, an additional 1 mg dose of glucagon from a new device or vial and syringe kit may be administered. For pediatric patients aged 2 to under 12 years of age, The recommended dose for pediatric patients who weigh less than 45 kg is 0.5 mg glucagon administered by subcutaneous injection into the lower abdomen, outer thigh, or outer upper arm. The recommended dose for pediatric patients who weigh 45 kg or greater is 1 mg glucagon administered by subcutaneous injection into the lower abdomen, outer thigh, or outer upper arm. If there has been no response after 15 minutes, an additional weight appropriate dose of glucagon from a new device or vial and syringe kit may be administered. Administer glucagon as soon as possible when severe hypoglycemia is recognized.

In other embodiment, for the adults and pediatric patients weighing 25 kg or more or for pediatric patients with unknown weight 6 years and older, the recommended dosage is 1 mg (1 mL) injected subcutaneously or intramuscularly into the upper arm, thigh, or buttocks, or intravenously. If there has been no response after 15 minutes, an additional 1 mg dose (1 mL) of glucagon may be administered using a new kit. For pediatric patients weighing less than 25 kg or for pediatric patients with unknown weight less than 6 years of age, the recommended dosage is 0.5 mg (0.5 mL) injected subcutaneously or intramuscularly into the upper arm, thigh, or buttocks, or intravenously. If there has been no response after 15 minutes, an additional 0.5 mg dose (0.5 mL) of glucagon may be administered.

In other embodiment, for adults for using glucagon as a diagnostic aid, the recommended dose for relaxation of the stomach, duodenal bulb, duodenum, and small bowel is 0.2 mg to 0.5 mg administered intravenously or 1 mg administered intramuscularly. Further, the recommended dose to relax the colon is 0.5 mg to 0.75 mg administered intravenously or 1 mg to 2 mg administered intramuscularly.

In one embodiment, the methods disclosed herein comprise administering to the patient a dose of glucagon intravenously or intramuscularly, wherein the glucagon is at a dose of about 0.1 mg to 10 mg. In some embodiments, the methods disclosed herein comprise administering to the patient a dose of glucagon intravenously or intramuscularly, wherein the glucagon is at a concentration of about 0.5 mg/0.1 mL or 10 mg/mL. In one embodiment, the intravenous dose is a bolus dose or an infusion.

In certain aspects, the inventive solutions described herein may be used to treat adults and adolescents (e.g., about 13-17 years). In certain aspects, the solutions described herein may be used as monotherapy or as adjunctive therapy.

The dosage levels can be dependent on the nature of the condition, drug efficacy, the condition of the patient, the judgment of the practitioner, and the frequency and mode of administration. The unit dosage forms can be administered to achieve any daily amount described herein, such as by administering one to five times daily (e.g., one, two, three, four, or five times daily).

EXAMPLES

The following examples are exemplary and not intended to be limiting. The present disclosure provides many different embodiments for implementing the features of the invention, and the following examples describe certain embodiments. It will be appreciated that other modifications and methods known to one of ordinary skill in the art can also be applied to the following experimental procedures, without departing from the scope of the invention.

Preparation of Different Types of Amino Acid-Hydrochloric Acid Solutions

Preparation of 1 mM Glycine hydrochloride solution: For example, 1.82 grams of hydrochloric acid (37%) was dissolved in 40 mL of dimethyl sulfoxide (DMSO). Then, 3.94 mg of glycine was added to the above DMSO-HCl solution under continuous stirring until a clear solution was obtained. The final volume was adjusted to 50 mL with DMSO.

Preparation of 1 mM Glutamic acid hydrochloride solution: For example, 800 mg of hydrochloric acid (37%) was dissolved into 20 mL of dimethyl sulfoxide (DMSO). Then, 3.7 mg of glutamic acid was added to the above DMSO-glutamic acid solution under continuous stirring until a clear solution was obtained. The final volume was adjusted to 25 mL with DMSO.

Preparation of 1 mM L-Aspartic acid hydrochloride solution: For example, 1.6 grams of hydrochloric acid (37%) was dissolved in 40 mL of dimethyl sulfoxide (DMSO). Then, 6.7 mg of L-aspartic acid was added to the above DMSO-aspartic acid solution under continuous stirring until a clear solution was obtained. The final volume was adjusted to 50 mL with DMSO.

General HPLC Procedure

As explained in detail below, the following HPLC procedure can be used to detect, quantify impurities of glucagon and to determine assay % of glucagon. The materials and general conditions are listed below:

TABLE 2

| Assay and related substances identification by HPLC chromatographic conditions | |
|---|---|
| Column | ACE C18, 150 mm × 3.0 mm, 3 μm. |
| Column Temperature | 45° C. |
| Flow rate | 0.5 mL/min |
| Detector | 214 nm with UV detector |
| Injection volume | 30 μL |
| Run time | 100 minutes |
| Sample temperature | 5° C. |
| Mode of elution | Gradient |
| Preparation of Mobile Phase A | Dissolved 16.3 g of monobasic potassium phosphate in 750 ml of water and adjusted pH to 2.7 with phosphoric acid. Further 800 mL of water and 200 mL of acetonitrile was added. |
| Preparation of Mobile Phase B | Prepare a mixture of Acetonitrile and water in 40:60% v/v ratio and degas by sonication for about 10 minutes. |

TABLE 3

| Gradient program | | |
|---|---|---|
| Time (minutes) | % Mobile phase-A | % Mobile phase-B |
| 0 | 68 | 32 |
| 65 | 68 | 32 |
| 70 | 10 | 90 |
| 80 | 10 | 90 |
| 90 | 68 | 32 |
| 100 | 68 | 32 |

Drug Substance Potency Correction:
Drug substance potency was corrected by using following formula $$API \text{ quantity required in } g = \frac{\text{Drug substance concentration (mg/mL)} * \text{Batch size}(L) * 100}{\text{Assay (HPLC, net) of } API}$$

Example 1

Glucagon solutions having the composition set forth in Table 4 were prepared.

TABLE 4

| Ingredients | Composition A | Composition B | Composition C |
|---|---|---|---|
| Glucagon | 5 mg | 5 mg | 5 mg |
| Trehalose dihydrate | 56 mg | 56 mg | 56 mg |
| 1 mM Glycine hydrochloride solution | 19.6 mg | — | — |
| 1 mM L-Glutamic acid hydrochloride solution | — | 20.42 mg | — |
| 1 mM L-Aspartic acid hydrochloride solution | — | — | 20 mg |
| DMSO | q.s. to 1 mL | q.s. to 1 mL | q.s. to 1 mL |
| pH of final solution | 3.6 | 3.6 | 3.6 |
| Concentration of Glycine | 0.017 mM/mL (0.00133 mg/mL) | — | — |
| Concentration of Glutamic acid | — | 0.018 mM/mL (0.0027 mg/mL) | — |
| Concentration of Aspartic acid | — | — | 0.202 mM/mL (0.0269 mg/mL) |
| Concentration of HCl | 5.808 mM/mL (0.5701 mg/mL) | 6.0534 mM/mL (0.5941 mg/mL) | 5.986 mM/mL (0.5876 mg/mL) |

Manufacturing Procedure of Compositions A, B and C

The specified quantity of DMSO was taken in a beaker. The required quantity of trehalose dihydrate was added to the beaker and stirred for about 10 minutes at 250±50 rpm to obtain a clear solution. The required quantity of 1 mM Glycine-Hydrochloride solution was added to the trehalose—DMSO solution with continuous stirring. The required quantity of glucagon was added to the above Glycine hydrochloride solution and stirred for about 10 minutes at 250±50 rpm to obtain a clear solution. The stability data for Compositions A, B and C was obtained, and is set forth in Table 5, 6 and 7 below.

TABLE 5

| | Composition A | | | | | |
|---|---|---|---|---|---|---|
| Major | | 25° C./60% RH | | 40° C./75% RH | | |
| degradants (at RRT) | Initial | 3 Months | 12 Months | 1 Month | 2 Months | 3 Months |
| 0.13 | — | 0.09 | 0.30 | 0.22 | 0.42 | 0.62 |
| 0.31 | 0.10 | 0.72 | 2.37 | 1.64 | 2.89 | 4.36 |
| 0.49 | — | 0.13 | 0.43 | 0.32 | 0.56 | 0.81 |
| 0.82 | — | 0.05 | 0.24 | 0.17 | 0.24 | 0.31 |
| 1.06 | — | 0.35 | 0.51 | — | — | 0.46 |
| 1.29 | — | 0.07 | 0.07 | 0.12 | 0.02 | 0.40 |
| 1.41 | — | — | 0.14 | — | 0.13 | 0.11 |
| Total Impurities | 0.32 | 1.80 | 5.65 | 2.93 | 6.61 | 8.84 |

— Means not detected

TABLE 6

| | Composition B | | | | | |
|---|---|---|---|---|---|---|
| Major | | 25° C./60% RH | | 40° C./75% RH | | |
| degradants (at RRT) | Initial | 2 Months | 3 Months | 1 Month | 2 Months | 3 Months |
| 0.13 | — | 0.06 | 0.09 | 0.21 | 0.41 | 0.60 |
| 0.31 | 0.09 | 0.47 | 0.72 | 1.55 | 2.85 | 4.23 |
| 0.49 | — | 0.10 | 0.12 | 0.31 | 0.54 | 0.77 |
| 0.82 | — | 0.04 | — | 0.06 | 0.09 | 0.11 |
| 1.06 | — | 0.23 | 0.22 | — | 0.31 | 0.33 |
| 1.29 | — | — | — | 0.10 | 0.28 | 0.35 |

TABLE 6-continued

| | Composition B | | | | | |
|---|---|---|---|---|---|---|
| Major | | 25° C./60% RH | | 40° C./75% RH | | |
| degradants (at RRT) | Initial | 2 Months | 3 Months | 1 Month | 2 Months | 3 Months |
| 1.41 | — | 0.06 | — | 0.19 | 0.17 | 0.30 |
| Total Impurities | 0.33 | 2.03 | — | 4.60 | 8.38 | 11.74 |

TABLE 7

| | Composition C | | | | | |
|---|---|---|---|---|---|---|
| Major | | 25° C./60% RH | | 40° C./75% RH | | |
| degradants (at RRT) | Initial | 2 Months | 3 Months | 1 Month | 2 Months | 3 Months |
| 0.13 | 0.04 | 0.08 | 0.09 | 0.22 | 0.41 | 0.61 |
| 0.31 | 0.22 | 0.53 | 0.61 | 1.45 | 2.88 | 4.16 |
| 0.49 | 0.05 | 0.10 | 0.09 | 0.28 | 0.51 | 0.73 |
| 0.82 | 0.03 | ND | ND | 0.06 | 0.11 | 0.11 |
| 1.06 | 0.18 | 0.25 | 0.25 | 0.33 | 0.38 | 0.46 |
| 1.29 | ND | 0.05 | 0.06 | ND | 0.22 | 0.31 |
| 1.41 | ND | ND | ND | 0.22 | 0.22 | 0.34 |
| Total Impurities | 1.30 | 2.43 | 2.39 | 4.88 | 8.37 | 11.75 |

ND = Not Detected

Example 2

Glucagon solutions having the compositions as set forth in Table 8 and 9 were prepared.

TABLE 8

| Ingredients | Composition D | Composition E | Composition F |
| --- | --- | --- | --- |
| Glucagon | 375 mg | 500 mg | 250 mg |
| Trehalose dihydrate | 4.2 gm | 5.6 gm | 2.8 gm |
| 1 mM Glycine hydrochloride solution | 4.18 gm | 1.96 gm | 565.34 mg |
| DMSO | 82.5 gm | 110 gm | 55 gm |
| pH | 3.0 | 3.7 | 4.0 |
| Concentration of Glycine | 0.050 mM/mL (0.0038 mg/mL) | 0.017 mM/mL (0.00133 mg/mL) | 0.0102 mM/mL (0.0007 mg/mL) |
| Concentration of HCl | 16.541 mM/mL (1.6236 mg/mL) | 5.808 mM/mL (0.5701 mg/mL) | 3.3509 mM/mL (0.3289 mg/mL) |

TABLE 9

| Ingredients | Composition G | Composition H |
| --- | --- | --- |
| Glucagon | 500 mg | 500 mg |
| Trehalose dihydrate | 5.6 gm | 5.6 gm |
| 1 mM Glycine hydrochloride solution | 1.11 gm | 615.28 mg |
| DMSO | 110 gm | 110 gm |
| pH of the final solution | 3.9 | 4.4 |
| Concentration of Glycine | 0.0100 mM/mL (0.0007 mg/mL) | 0.005 mM/mL (0.0004 mg/mL) |
| Concentration of HCl | 3.7419 mM/mL (0.3673 mg/mL) | 1.823 mM/mL (0.1789 mg/mL) |

Manufacturing Procedure of Compositions D, E, F, G and H

The specified quantity of DMSO was taken in a glass Duran bottle. Then, the required quantity of trehalose dihydrate was added to the glass Duran bottle and stirred for about 10 minutes at 250±50 rpm to obtain a clear solution. The required quantity of 1 mM glycine hydrochloride solution was added to the trehalose-DMSO solution with continuous stirring. The required quantity of glucagon was added to the above glycine hydrochloride solution and stirred for about 10 minutes at 250±50 rpm to obtain a clear solution and filled in vials. Stability was tested, and the data for Compositions D, F, F, and G are set forth in Table 10, 11, 12 and 13 below.

TABLE 10

| | Composition D | | |
| --- | --- | --- | --- |
| Major degradants (at RRT) | Initial | 25° C./ 60% RH 1 Month | 40° C./ 75% RH 1 Month |
| Assay | 96.6 | 79.6 | 41.9 |
| 0.13 | 0.05 | 0.12 | 1.14 |
| 0.31 | ND | 0.18 | 0.79 |
| 0.49 | ND | 0.06 | 0.22 |
| 0.82 | ND | 0.06 | 0.1 |
| 1.06 | ND | 0.14 | 0.6 |
| 1.29 | ND | ND | ND |
| 1.41 | ND | 0.31 | 2.89 |
| Total Impurities | 4.92 | 18.90 | 53.00 |

TABLE 11

| | Composition E | | | |
| --- | --- | --- | --- | --- |
| Major degradants (at RRT) | Initial | 25° C./ 60% RH 1 Month | 25° C./ 60% RH 6 Month | 40° C./ 75% RH 1 Month | 40° C./ 75% RH 6 Month |
| Assay | 100.3 | 104.4 | — | 100.2 | — |
| 0.13 | ND | 0.03 | 0.15 | 0.20 | 1.26 |
| 0.31 | ND | 0.23 | 1.15 | 1.47 | 8.36 |
| 0.49 | ND | ND | 0.20 | 0.3 | 1.50 |
| 0.82 | ND | ND | — | 0.19 | 1.13 |
| 1.06 | ND | ND | 0.1 | ND | 1.80 |
| 1.29 | ND | ND | 0.18 | ND | 0.78 |
| 1.41 | ND | ND | — | 0.07 | 0.26 |
| Total Impurities | 0.0 | 0.56 | 2.51 | 2.90 | 18.46 |

TABLE 12

| | Composition F | | | |
| --- | --- | --- | --- | --- |
| Major degradants (at RRT) | Initial | 25° C./ 60% RH 6 Month | 25° C./ 60% RH 12 Month | 40° C./ 75% RH 1 Month | 40° C./ 75% RH 6 Month |
| Assay | 98.9 | — | 95 | 97.9 | — |
| 0.13 | ND | 0.14 | 0.27 | 0.19 | 1.11 |
| 0.31 | ND | 0.47 | 0.88 | 0.65 | 3.38 |
| 0.49 | ND | 0.19 | 0.36 | 0.27 | 1.31 |
| 0.62 | ND | — | — | ND | — |
| 0.81 | ND | 0.86 | 1.42 | 1.23 | 6.30 |
| 0.96 | ND | 0.06 | 0.02 | 0.11 | — |
| 1.07 | ND | 0.34 | 0.24 | ND | 1.38 |
| 1.09 | ND | — | — | ND | — |
| 1.31 | ND | — | 0.04 | ND | 0.18 |
| 1.42 | ND | — | — | ND | 0.06 |
| 1.69 | ND | 0.1 | 0.19 | 0.14 | 0.76 |
| Total Impurities | 0.0 | 2.41 | 4.46 | 3.00 | 18.14 |

TABLE 13

| | Composition G | | | |
| --- | --- | --- | --- | --- |
| Major degradants (at RRT) | Initial | 25° C./ 60% RH 6 Month | 25° C./ 60% RH 12 Month | 40° C./ 75% RH 3 Month | 40° C./ 75% RH 6 Month |
| Assay | 104.9 | 99.6 | 97.6 | 87.6 | 80.2 |
| 0.13 | ND | 0.15 | 0.28 | 0.57 | 1.13 |
| 0.31 | ND | 0.68 | 1.22 | 2.42 | 4.49 |
| 0.49 | ND | 0.22 | 0.35 | 0.77 | 1.38 |
| 0.62 | ND | — | — | — | — |
| 0.81 | 0.05 | 0.75 | 1.16 | 2.83 | 5.18 |
| 0.96 | ND | 0.05 | 0.03 | 0.04 | 0.22 |
| 1.07 | ND | 0.36 | 0.19 | 0.57 | 1.22 |
| 1.09 | ND | 0.36 | — | 0.04 | — |
| 1.31 | ND | 0.02 | 0.03 | 0.05 | 0.05 |
| 1.42 | ND | — | — | — | 0.05 |
| 1.69 | ND | 0.06 | 0.15 | 0.28 | 0.59 |
| Total Impurities | 0.20 | 2.57 | 3.85 | 8.28 | 16.98 |

Example 3

Glucagon solution having the compositions set forth in Table 14 were prepared, and tested for stability in pre-filled syringe (PFS). The stability results are shown in Tables 15 and 16.

TABLE 14

| Ingredients | Composition I | Composition J | Composition K |
| --- | --- | --- | --- |
| Glucagon | 500 mg | 375 mg | 375 mg |
| Trehalose dihydrate | 5.60 gm | 4.2 gm | 4.2 gm |

TABLE 14-continued

| Ingredients | Composition I | Composition J | Composition K |
|---|---|---|---|
| 1 mM Glycine hydrochloride solution | 813.95 mg | 828.35 mg | 1.13 gm |
| DMSO | 110 gm | 82.5 gm | 82.5 gm |
| pH | 4.0 | 3.9 | 3.7 |
| Concentration of Glycine | 0.007 mM/mL (0.00055 mg/mL) | 0.0100 mM/mL (0.0007 mg/mL) | 0.01374 mM/mL (0.0010 mg/mL) |
| Concentration of HCl | 2.743 mM/mL (0.2693 mg/mL) | 3.723 mM/mL (0.365 mg/mL) | 5.0972 mM/mL (0.5003 mg/mL) |

TABLE 15

|  | Composition I | | Composition J | |
|---|---|---|---|---|
| Major degradants (at RRT) | 25° C./ 60% RH 6 Month | 40° C./ 75% RH 6 Month | 25° C./ 60% RH 6 Month | 40° C./ 75% RH 6 Month |
| Assay | 96.1 | 74.8 | 87.5 | 67.8 |
| 0.13 | 0.14 | 1.15 | 0.15 | 1.22 |
| 0.31 | 0.47 | 3.42 | 0.71 | 5.19 |
| 0.49 | 0.21 | 1.38 | 0.21 | 1.48 |
| 0.60 | — | 0.12 | — | 0.13 |
| 0.81 | — | 6.54 | 0.70 | 4.84 |
| 0.96 | — | 0.14 | 0.56 | 0.17 |
| 1.07 | — | 2.39 | 0.04 | 2.42 |
| 1.31 | — | — | — | 0.08 |
| 1.42 | — | — | — | 0.29 |
| 1.69 | — | 0.67 | 0.06 | 0.59 |
| Total Impurities | 3.12 | 20.95 | 2.76 | 19.8 |

TABLE 16

|  | Composition K | |
|---|---|---|
| Major degradants (at RRT) | 25° C./ 60% RH 6 Month | 40° C./ 75% RH 6 Month |
| Assay | 87.2 | 65.7 |
| 0.13 | 0.15 | 1.31 |
| 0.31 | 1.17 | 8.41 |
| 0.49 | 0.07 | 1.57 |
| 0.60 | — | — |
| 0.81 | 0.20 | 1.28 |
| 0.96 | 0.84 | 0.35 |
| 1.07 | 0.04 | 0.18 |
| 1.31 | — | — |
| 1.42 | — | 0.16 |
| 1.69 | 0.05 | 0.5 |
| Total Impurities | 3.39 | 20.25 |

Example 4

Glucagon solution having a Comparative Composition are set forth in Table 17 below.

TABLE 17

| Ingredients | Comparative Composition |
|---|---|
| Glucagon | 375 mg |
| Trehalose dihydrate | 4.16 gm |
| 1N Sulfuric acid | 450 mg |
| DMSO | 82.5 gm |
| pH | 3.65 |

Example 5

Circular dichroism (CD) is dichroism involving circularly polarized light, i.e., the differential absorption of left- and right-handed light. Left-hand circular (LHC) and right-hand circular (RHC) polarized light represent two possible spin angular momentum states for a photon, and so circular dichroism is also referred to as dichroism for spin angular momentum Circular Dichroism Results:

| Sample Details | α-helix (%) | β (%)- Anti- parallel pleated sheet | Random Coil (%) | Turn (%) |
|---|---|---|---|---|
| GVOKE ®-Lot: 20006C (Exp: April 2022) | 0.0 | 31.8 | 45.6 | 22.5 |
| Composition A (Initial) | 0.0 | 30.6 | 45.6 | 23.7 |

The above data shows that the secondary structure of Composition A is similar to Comparative Composition (GVOKE®).

Intrinsic Fluorescence Results:

Intrinsic Fluorescence is highly sensitive to changes in the polarity of the local environment of tryptophan residues that may accompany subtle tertiary structure (Higher order structure) alterations.

| Sample Details | Wavelength MAX | Intensity |
|---|---|---|
| GVOKE-Lot: 20006C (Exp: April 2022) | 342 | 396.563 |
| Composition A (Initial) | 343 | 442.954 |
| Composition A (25° C./60% RH-1 Month) | 342 | 432.816 |

The emission spectra of Composition A and GVOKE® revealed that they share the same wavelength maximum. Additionally, both Composition A and GVOKE® exhibited identical intensity levels at this maximum wavelength. These observations suggested that Composition A (Initial & 25° C./60% RH-1 Month) and GVOKE® possess a similar higher order structure.

Having now fully described this invention, it will be understood by those of ordinary skill in the art that it can be performed within a wide equivalent range of parameters without affecting the scope of the invention or any embodiment thereof. All publications, patent applications and patents disclosed herein are incorporated by reference in their entirety.

What is claimed is:

1. An injectable solution, consisting of:
   (a) a therapeutically effective amount of glucagon;
   (b) at least one pharmaceutically acceptable solvent;
   (c) at least one stabilizing agent;
   (d) at least one sugar; and
   (e) optionally, at least one pH adjusting agent;
   wherein the solution does not comprise a surfactant,
   wherein said injectable solution is stable and ready-to-use,
   wherein pH of said solution ranges from 3.8 to 4.2,
   wherein the concentration of glucagon in the injectable solution is from about 2.5 mg/mL to about 10 mg/mL,
   wherein the total impurities are present in an amount less than 10% w/w when stored at 25° C./60% RH for at least 12 months,
   wherein a Glucagon (16-29) impurity is present in an amount less than 2% w/w when stored at 25° C./60% RH for at least 12 months,
   wherein the injectable solution is suitable for administration for at least 12 months, and
   wherein the injectable solution has not been reconstituted from a lyophilized powder prior to administration.

2. The injectable solution according to claim 1, wherein a concentration of glucagon is 0.5 mg/0.1mL eq.

3. The injectable solution according to claim 1, wherein the at least one pharmaceutically acceptable solvent is dimethyl sulfoxide (DMSO); dimethylformamide (DMF); ethyl acetate; n-methyl pyrrolidone (NMP); 1-methyl-2-pyrrolidone; 1,3-dimethyl-2-imidazolidinone; dimethylacetamide (DMA); acetone; tetrahydrofuran; 1,4-dioxane; acetonitrile;
and propylene carbonate; or mixtures thereof.

4. The injectable solution according to claim 1, wherein the at least one pharmaceutically acceptable solvent is dimethyl sulfoxide (DMSO).

5. The injectable solution according to claim 1, wherein the at least one stabilizing agent is present in a concentration between 0.001 mM and 50 mM.

6. The injectable solution according to claim 1, wherein the at least one stabilizing agent is present in a concentration between 0.001 mM and 10 mM.

7. An injectable solution consisting of:
   (a) a therapeutically effective amount of glucagon;
   (b) dimethyl sulfoxide as a pharmaceutically acceptable solvent;
   (c) at least one stabilizing agent is selected from glycine, ethyl glycine, glycylglycine, alanine, β-alanine, valine, leucine, norleucine, isoleucine, serine, threonine, aspartic acid, glutamic acid, hydroxy glutamic acid, lysine, hydroxylysine, ornithine, arginine, methionine, asparagine, glutamine, taurine, creatinine, ethylenediaminetetraacetic acid, trimethylglycine (betaine), glycine hydrochloride, trimethylglycine (betaine) hydrochloride, or mixtures thereof,
   (d) trehalose; and
   (e) optionally, at least one pH adjusting agent;
   wherein said injectable solution is stable and ready-to-use,
   wherein pH of said solution ranges from 3.8 to 4.2,
   wherein the concentration of glucagon in the injectable solution is from about 2.5 mg/mL to about 10 mg/mL,
   wherein the total impurities are present in an amount less than 10% w/w when stored at 25° C./60% RH for at least 12 months,
   wherein a Glucagon (16-29) impurity is present in an amount less than 2% w/w when stored at 25° C./60% RH for at least 12 months, and
   wherein the injectable solution has not been reconstituted from a lyophilized powder prior to administration.

8. The injectable solution according to claim 1, wherein the at least one stabilizing agent is glycine, ethylglycine, glycylglycine, alanine, β-alanine, valine, leucine, norleucine, isoleucine, serine, threonine, aspartic acid, glutamic acid, hydroxy glutamic acid, lysine, hydroxylysine, ornithine, arginine, methionine, asparagine, glutamine, taurine, creatinine, ethylenediaminetetraacetic acid, trimethylglycine (betaine), glycine hydrochloride, trimethylglycine (betaine) hydrochloride, or mixtures thereof.

9. The injectable solution according to claim 1, wherein the at least one stabilizing agent is glycine hydrochloride.

10. The injectable solution according to claim 1, wherein the at least one sugar is trehalose, lactose, glucose, sucrose, inositol, fructose, or mixtures thereof.

11. The injectable solution according to claim 1, wherein the at least one sugar is trehalose.

12. The injectable solution according to claim 1, wherein the at least one pH adjusting agent is present, and selected from hydrochloric acid, sodium hydroxide, potassium hydroxide, magnesium hydroxide, sodium carbonate, and tromethamine.

13. A sealed container comprising the injectable solution according to claim 1, wherein the sealed container is selected from an ampoule, a vial, a pre-filled syringe (PFS) or an auto-injector.

14. A method of treatment, comprising administering a therapeutically effective amount of the injectable solution according to claim 1 to a patient in need of treatment for Hypoglycemia, Exercise-Induced Hypoglycemia ("EIH") in diabetes, Post-Bariatric-Hypoglycemia ("PBH"), Congenital Hyperinsulinism ("CHI") or Non-Insulinoma Pancreatogenous Hypoglycaemia Syndrome ("NIPHS").

15. The method of treatment according to claim 14, wherein the injectable solution is suitable for subcutaneous, intravenous or intramuscular administration.

16. An injectable solution, consisting of:
(a) a therapeutically effective amount of glucagon;
(b) at least one pharmaceutically acceptable solvent;
(c) at least one stabilizing agent;
(d) at least one sugar; and
(e) optionally, at least one pH adjusting agent;
wherein the solution does not comprise a surfactant,
wherein said injectable solution is stable and ready-to-use,
wherein pH of said solution ranges from 3.8 to 4.2,
wherein the concentration of glucagon in the injectable solution is from about 2.5 mg/mL to about 10 mg/mL,
wherein the total impurities are present in an amount less than 10% w/w when stored at 25° C./60% RH for at least 12 months,
wherein a Glucagon (16-29) impurity is present in an amount less than 2% w/w when stored at 25°° C./60% RH for at least 12 months, and
wherein the injectable solution has not been reconstituted from a lyophilized powder prior to administration.

17. The injectable solution according to claim 7, wherein the at least one stabilizing agent is present in a concentration between 0.001 mM and 50 mM.

18. The injectable solution according to claim 7, wherein the at least one pH adjusting agent is present, and selected from hydrochloric acid, sodium hydroxide, potassium hydroxide, magnesium hydroxide, sodium carbonate, and tromethamine.

19. A sealed container comprising the injectable solution according to claim 7, wherein the sealed container is selected from an ampoule, a vial, a pre-filled syringe (PFS) or an auto-injector.

20. A method of treatment, comprising administering a therapeutically effective amount of the injectable solution according to claim 7 to a patient in need of treatment for Hypoglycemia, Exercise-Induced Hypoglycemia ("EIH") in diabetes, Post-Bariatric Hypoglycemia ("PBH"), Congenital Hyperinsulinism ("CHI") or Non-Insulinoma Pancreatogenous Hypoglycaemia Syndrome ("NIPHS").

* * * * *

SEQUENCE LISTING

```
Sequence total quantity: 1
SEQ ID NO: 1            moltype = AA  length = 29
FEATURE                 Location/Qualifiers
REGION                  1..29
                        note = Synthetic: full Glucagon polypeptide
source                  1..29
                        mol_type = protein
                        organism = synthetic construct
SEQUENCE: 1
HSQGTFTSDY SKYLDSRRAQ DFVQWLMNT                                             29
```